(12) United States Patent
Matsushita et al.

(10) Patent No.: US 9,714,907 B2
(45) Date of Patent: Jul. 25, 2017

(54) METHOD AND APPARATUS FOR MEASURING SCATTERING INTENSITY DISTRIBUTION

(71) Applicant: Inter-University Research Institute Corporation High Energy Accelerator Research Organization, Ibaraki (JP)

(72) Inventors: Tadashi Matsushita, Ibaraki (JP); Wolfgang Voegeli, Ibaraki (JP); Tetsuro Shirasawa, Chiba (JP); Toshio Takahashi, Tokyo (JP); Etsuo Arakawa, Tokyo (JP)

(73) Assignee: Inter-University Research Institute Corporation High Energy Accelerator Research Organization, Ibaraki (JP)

(*) Notice: Subject to any disclaimer, the term of this patent is extended or adjusted under 35 U.S.C. 154(b) by 226 days.

(21) Appl. No.: 14/651,813

(22) PCT Filed: Dec. 10, 2013

(86) PCT No.: PCT/JP2013/083064
§ 371 (c)(1),
(2) Date: Nov. 18, 2015

(87) PCT Pub. No.: WO2014/092073
PCT Pub. Date: Jun. 19, 2014

(65) Prior Publication Data
US 2016/0069825 A1    Mar. 10, 2016

(30) Foreign Application Priority Data

Dec. 14, 2012 (JP) ................................. 2012-273064

(51) Int. Cl.
*G01N 23/20* (2006.01)

(52) U.S. Cl.
CPC ....... *G01N 23/20008* (2013.01); *G01N 23/20* (2013.01); *G21K 2201/062* (2013.01); *G21K 2201/064* (2013.01)

(58) Field of Classification Search
CPC .... G01N 23/207; G01N 23/20; G01N 23/201; G01N 2223/054
See application file for complete search history.

(56) References Cited

U.S. PATENT DOCUMENTS

| 5,923,720 A * | 7/1999 | Barton .................. B82Y 10/00 378/83 |
| 2014/0307854 A1* | 10/2014 | Lauridsen ............ G01N 23/207 378/73 |

(Continued)

OTHER PUBLICATIONS

Extended European Search Report issued in corresponding EP Application No. 13862246.9, dated Jun. 29, 2016, pp. 1-6.

(Continued)

*Primary Examiner* — Hoon Song
(74) *Attorney, Agent, or Firm* — MKG LLC

(57) ABSTRACT

It is an object of the present invention to provide a method and an apparatus for measuring a scattering intensity distribution capable of measuring a scattering intensity distribution in a reciprocal space in a short time. The method or apparatus for measuring a scattering intensity distribution causes X-rays emitted from an X-ray source (101) to be reflected by an X-ray optical element (102) so as to converge in the vicinity of a surface of a sample (SA), causes monochromatic X-rays condensed after passing through a plurality of optical paths to be incident on the sample at glancing angles ($\omega$) that differ depending on the respective optical paths at a time in a state in which there is a correlation between an angle formed by each optical path of the monochromatic X-rays and a reference plane, and an angle formed by each optical path and a plane including the (Continued)

normal of the reference plane and an optical path located in the center of the respective optical paths, detects scattering intensities of the monochromatic X-rays scattered by the sample using a two-dimensional detector (103) and calculates a scattering intensity distribution in the reciprocal space based on the scattering intensity distribution detected by the two-dimensional detector and the correlation.

12 Claims, 9 Drawing Sheets

(56) References Cited

U.S. PATENT DOCUMENTS

| 2015/0003592 A1* | 1/2015 | Beckers | G01N 23/205 |
| | | | 378/74 |
| 2015/0204802 A1* | 7/2015 | Pois | G01N 23/201 |
| | | | 378/86 |

OTHER PUBLICATIONS

International Search Report issued in corresponding PCT Application No. PCT/JP2013/083064, dated Mar. 11, 2014, pp. 1-2.

* cited by examiner

METHOD AND APPARATUS FOR MEASURING SCATTERING INTENSITY DISTRIBUTION

TECHNICAL FIELD

The present invention relates to a method and an apparatus for measuring a scattering intensity distribution in a reciprocal space by irradiating a sample with X-rays.

BACKGROUND ART

In recent years, studies are being actively carried out on quantum well structures having physical properties different from those of general crystal materials. For example, superlattice semiconductors including laminated semiconductor thin-films exhibit a band structure that varies depending on the period (thickness) of layers and type of atoms, and therefore applications to a variety of devices is expected. In a quantum dot which is a three-dimensional quantum confinement structure, a density of states is discretized and concentration occurs on a specific state, and it is thereby theoretically possible to implement a laser medium with extremely high efficiency. Physical properties of such a quantum well structure fluctuate a great deal depending on a period of crystal lattice and a degree of disorder or the like, and so it is necessary to acquire accurate information on the crystal lattice when evaluating those properties.

To evaluate regularity of the crystal lattice, a method is used which irradiates a sample with X-rays and measures a scattering intensity distribution in a reciprocal space. According to this method which is also called "reciprocal space mapping" or "reciprocal space map," a scattering intensity of X-rays in the vicinity of reciprocal lattice points is mapped and a scattering power distribution is obtained. With an ideal crystal structure, the diffraction intensity of X-rays becomes stronger only at reciprocal lattice points, but when there is disorder in a crystal lattice, significant scattering power is observed also at positions away from reciprocal lattice points.

The basic concept of reciprocal space mapping will be described. First, a relationship between a real space and a reciprocal space will be described in brief. FIG. 6 is a schematic view illustrating a relationship between a real space and a reciprocal space in a two-dimensional crystal. FIG. 6A shows a crystal lattice made up of atoms A1 to A4. In this crystal lattice, for example, the lattice spacing of a 100-plane is $d_{100}$, the lattice spacing of a 010-plane is $d_{010}$ and the lattice spacing of a 110-plane is duo.

When the crystal lattice in FIG. 6A is transformed into a reciprocal space, the transformed crystal lattice appears as shown in FIG. 6B. The reciprocal space corresponds to a Fourier transform of a real space and a reciprocal lattice point includes information of the crystal lattice in the real space. For example, as shown in FIG. 6B, the distance between an origin O of the reciprocal space and a certain reciprocal lattice point corresponds to a reciprocal of the lattice spacing of the corresponding crystal plane. To be more specific, the distance between the origin O of the reciprocal space and the point 100 corresponds to the reciprocal $1/d_{100}$ of the lattice spacing $d_{100}$ of the 100-plane, and the distance between the origin O of the reciprocal space and the point 010 corresponds to the reciprocal $1/d_{010}$ of the lattice spacing $d_{010}$ of the 010-plane.

FIG. 7 is a schematic view illustrating a relationship between a reciprocal lattice point and an Ewald sphere. FIG. 7 illustrates a reciprocal space corresponding to a three-dimensional crystal when seen from a qy-axis (not shown) direction perpendicular to the plane including a qx-axis and a qz-axis. In FIG. 7, a $K_0$ vector represents a wave number vector of incident X-rays incident upon the crystal structure and a K vector represents a wave number vector of scattered X-rays scattered by the crystal structure. In FIG. 7, a plurality of regularly arranged white circle marks represent reciprocal lattice points.

The scattering intensity of X-rays by an ideal crystal structure without crystal lattice disorder becomes stronger under a condition that a reciprocal lattice point exists on a spherical surface of the Ewald sphere $E_0$ having a radius $(2\pi/\lambda)$, $2\pi$ times the reciprocal of wavelength ($\lambda$) of X-rays. In this case, X-rays are scattered in a projected pattern obtained by projecting reciprocal lattice points located on the spherical surface of the Ewald sphere $E_0$ from the center of the Ewald sphere $E_0$. When there is crystal lattice disorder, the scattering intensity becomes stronger also at points other than the reciprocal lattice points according to the degree of the disorder. For this reason, it is possible to evaluate regularity of the crystal lattice by calculating a scattering intensity distribution through reciprocal lattice mapping.

To be more specific, for example, when a plurality of crystal lattices having different intervals are mixed in a sample and reciprocal lattice points on the qz-axis are located on the Ewald sphere, scattering power appears along a straight line connecting the origin and the reciprocal lattice points (qz-axis direction in FIG. 7). On the other hand, when a plurality of crystal planes (lattice planes) having different inclinations are mixed in a sample, scattering power appears in a direction orthogonal to a straight line connecting the origin and a reciprocal lattice point in the reciprocal space (q'x-axis direction in FIG. 7). Thus, by checking the distribution of scattering power, it is possible to evaluate regularity of the crystal lattice.

In reciprocal space mapping, a scattering intensity distribution of X-rays in the vicinity of a target reciprocal lattice point is normally measured. FIG. 8 is a schematic view illustrating an example of a measuring apparatus used for reciprocal lattice mapping. In a measuring apparatus 2 shown in FIG. 8, -monochromatic (single wavelength) X-rays that are emitted from an X-ray source 201 and passed through a monochromator 202 is incident on a sample 203 at a glancing angle (complementary angle of an angle of incidence) ω. X-rays scattered at the sample 203 is incident on a detector 205 via a collimator 204. The collimator 204 selectively guides only X-rays scattered toward a 2θ direction from the sample to the detector 205.

An example of the measuring mode of reciprocal space mapping using the measuring apparatus 2 is ω scanning. In ω scanning, ω is changed with 2θ fixed to a predetermined value and a scattering intensity distribution in the ω direction is scanned. Through this scanning in the ω direction, a scattering power distribution in the direction substantially orthogonal to the straight line connecting the origin and the reciprocal lattice point in the reciprocal space (q'x-axis direction in FIG. 7) is detected. When scanning in the ω direction for a certain 2θ is finished, the value of 2θ is slightly changed and scanning in the ω direction is performed again. Selecting a different value of 2θ has a meaning equivalent to selecting a different qz position along the qz-axis of the reciprocal space. In this way, by repeating scanning in the ω direction every time the value of 2θ is changed, it is possible to obtain a scattering power distribution in a region RSM within the qx-qz plane, that is, a two-dimensional scattering intensity distribution corresponding to a reciprocal space map.

Another example of the measuring mode is $\omega$-$2\theta$ scanning. In this measuring mode, a scattering intensity distribution is scanned so that the amount of change $\Delta\omega$ of $\omega$ and the amount of change $\Delta(2\theta)$ of $2\theta$ always satisfy a relationship of $\Delta\omega:\Delta(2\theta)=1:2$. Furthermore, the above scanning is repeated every time the initial value $\omega_0$ of $\omega$ is changed. Scanning that satisfies $\Delta\omega:\Delta(2\theta)=1:2$ corresponds to measuring a scattering power distribution in a straight line direction that passes through a given point of the reciprocal space and the origin. Changing $\omega_0$ corresponds to specifying a different position on the q'x-axis. Thus, by repeating $\omega$-$2\theta$ scanning every time $\omega_0$ is changed, it is possible to measure the scattering power distribution within the region RSM in FIG. 7.

FIG. 9 is a schematic view illustrating another example of the measuring apparatus used for reciprocal space mapping. In a measuring apparatus 3 shown in FIG. 9, monochromatic X-rays that are emitted from an X-ray source 301 and passed through a monochrometor 302 enter a sample 303 at a glancing angle $\omega$. X-rays scattered at the sample 303 is incident on a one-dimensional detector 305. The one-dimensional detector 305 is configured so as to be able to measure a wide scattering angle ($2\theta$ direction) simultaneously. For this reason, scanning in the $2\theta$ direction is not necessary in reciprocal space mapping using the measuring apparatus 3.

SUMMARY OF INVENTION

The method for measuring a scattering intensity distribution using the measuring apparatus shown in FIG. 8 requires scanning in both the glancing angle direction ($\omega$ direction) and the scattering angle direction ($2\theta$ direction). According to the method for measuring a scattering intensity distribution using the measuring apparatus shown in FIG. 9, it is necessary to perform at least scanning in the glancing angle direction ($\omega$ direction) and measure the scattering intensity under a plurality of conditions with different glancing angle ($\omega$) values. For this reason, there is a problem that it takes a long time to obtain one scattering intensity distribution (typically, several minutes to several hours).

The present invention has been implemented in view of the above problems, and it is an object of the present invention to provide a method and an apparatus for measuring a scattering intensity distribution capable of measuring a scattering intensity distribution in a reciprocal space in a short time.

A method for measuring a scattering intensity distribution, according to present invention includes reflecting X-rays emitted from an X-ray source by an X-ray optical element so as to converge in a vicinity of a surface of a sample, causing monochromatic X-rays to pass through a plurality of optical paths to the sample at glancing angles that differ depending on the respective optical paths, at a time with correlation that a plane along which the X-rays propagate is inclined at a given angle with respect to a reference plane and is inclined at a given angle with respect to a plane including a central optical path among the optical paths and a normal of the reference plane, detecting scattering intensities of the monochromatic X-rays scattered by the sample using a two-dimensional detector, and coordinate-transforming the scattering intensities detected by the two-dimensional detector based on the correlation thereby to measure the scattering intensity distribution in a reciprocal space.

According to this configuration, monochromatic X-rays having a predetermined correlation are caused to be incident on the sample at different glancing angles at a time and scattering intensities of the monochromatic X-rays scattered by the sample are detected using the two-dimensional detector, which eliminates the need for scanning in both the glancing angle direction ($\omega$ direction) and the scattering angle direction ($2\theta$ direction). That is, monochromatic X-rays with a predetermined correlation are caused to be incident on the sample at different glancing angles at a time, and it is thereby possible to cause scattering corresponding to a plurality of conditions with different glancing angles to occur at a time, and it is thereby possible to detect scattering corresponding to a plurality of conditions with different glancing angle and scattering angle values at a time using the two-dimensional detector. Thus, it is possible to calculate a scattering intensity distribution in a reciprocal space based on the scattering intensity distribution and the correlation detected by the two-dimensional detector. That is, it is no longer necessary to perform scanning in both the glancing angle direction ($\omega$ direction) and the scattering angle direction ($2\theta$ direction) and it is possible to measure a scattering intensity distribution in a reciprocal space in a short time.

Since the plane along which the X-rays propagate is inclined at a given angle with respect to the reference plane and the plane including the optical path located in the center of the respective optical paths and the normal of the reference plane, it is possible to cause scattering corresponding to a plurality of conditions with different glancing angle and scattering angle values to occur at a time and calculate a scattering intensity distribution in a reciprocal space based on the inclination of the X-ray beam with respect to the reference plane.

In the method for measuring a scattering intensity distribution of the present invention, it is preferable to arrange the X-ray source, the X-ray optical element, and the sample along an identical circumference. This configuration allows X-rays emitted from the X-ray source to converge by the X-ray optical element and to be incident on the sample appropriately.

In the method for measuring a scattering intensity distribution of the present invention, the reference plane may be a plane including the circumference. The reference plane may also be the surface of the sample.

In the method for measuring a scattering intensity distribution of the present invention, characteristic X-rays are preferably used as the X-rays. In this configuration, compared to the case where white X-rays from synchrotron radiation or the like are used, the X-ray source configuration is simplified and the cost involved with the measurement of the scattering intensity distribution can be reduced. The need for upsizing the measuring apparatus can be eliminated compared to the case where white X-rays from synchrotron radiation or the like are used.

In the method for measuring a scattering intensity distribution of the present invention, it is preferable to use a doubly-curved crystal or bent-twisted crystal as the X-ray optical element. This configuration makes it easier for monochromatic X-rays to be incident on the sample at different glancing angle at a time.

A measuring apparatus according to the present invention includes an X-ray source, an X-ray optical element reflecting X-rays emitted from an X-ray source so as to converge in a vicinity of a surface of a sample, a two-dimensional detector detecting the scattering intensities of the monochromatic X-rays scattered by the sample, a calculation section which coordinate-transforms the scattering intensities detected by the two-dimensional detector based on the correlation thereby to measure the scattering intensity distribution in a reciprocal space, and wherein monochromatic X-rays cause to pass through a plurality of optical paths to the sample at glancing angles that differ depending on the respective optical paths, at a time with correlation that a plane along which the X-rays propagate is inclined at a given angle with respect to a reference plane and is inclined at a given angle with respect to a plane including a central optical path among the optical paths and a normal of the reference plane.

According to this configuration, monochromatic X-rays having a predetermined correlation are caused to be incident on the sample at different glancing angles at a time and scattering intensities of the monochromatic X-rays scattered by the sample are detected using the two-dimensional detector, which eliminates the need for scanning in both the glancing angle direction (ω direction) and the scattering angle direction (2θ direction). It is thereby possible to measure a scattering intensity distribution in a reciprocal space in a short time.

Since the plane in which the X-ray beam propagates is inclined at a given angle with respect to the reference plane and the plane including the optical path located in the center of the respective optical paths and the normal of the reference plane, the X-ray beam is diagonally incident upon the reference plane and it is thereby possible to cause scattering corresponding to a plurality of conditions with different glancing angle and scattering angle values to occur at a time and calculate a scattering intensity distribution in a reciprocal space based on the inclination of the X-ray beam with respect to the reference plane.

In the measuring apparatus of the present invention, it is preferable to arrange the X-ray source, the X-ray optical element and the sample along an identical circumference. This configuration allows X-rays emitted from the X-ray source to converge by the X-ray optical element and be incident on the sample appropriately.

In the measuring apparatus of the present invention, the reference plane may be a plane including the circumference. The reference plane may also be the surface of the sample.

In the measuring apparatus of the present invention, the X-ray source is preferably configured to be able to generate characteristic X-rays. In this configuration, compared to the case where white X-rays from synchrotron radiation or the like are used, the X-ray source configuration is simplified and the cost involved with the measurement of the scattering intensity distribution can be reduced.

In the measuring apparatus of the present invention, it is preferable to use a doubly-curved crystal or bent-twisted crystal as the X-ray optical element. This configuration makes it easier for monochromatic X-rays to be incident on the sample at different glancing angles at a time.

According to the present invention, it is possible to provide a method and an apparatus for measuring a scattering intensity distribution capable of measuring a scattering intensity distribution in a reciprocal space in a short time.

DETAILED DESCRIPTION

Hereinafter, a method and an apparatus for measuring a scattering intensity distribution in a reciprocal space according to an embodiment of the present invention will be described with reference to the accompanying drawings. Although a simplified measuring apparatus will be described to describe the present invention below, it is assumed that the present apparatus is provided with a configuration enough for a normal measuring.

Figure 1:
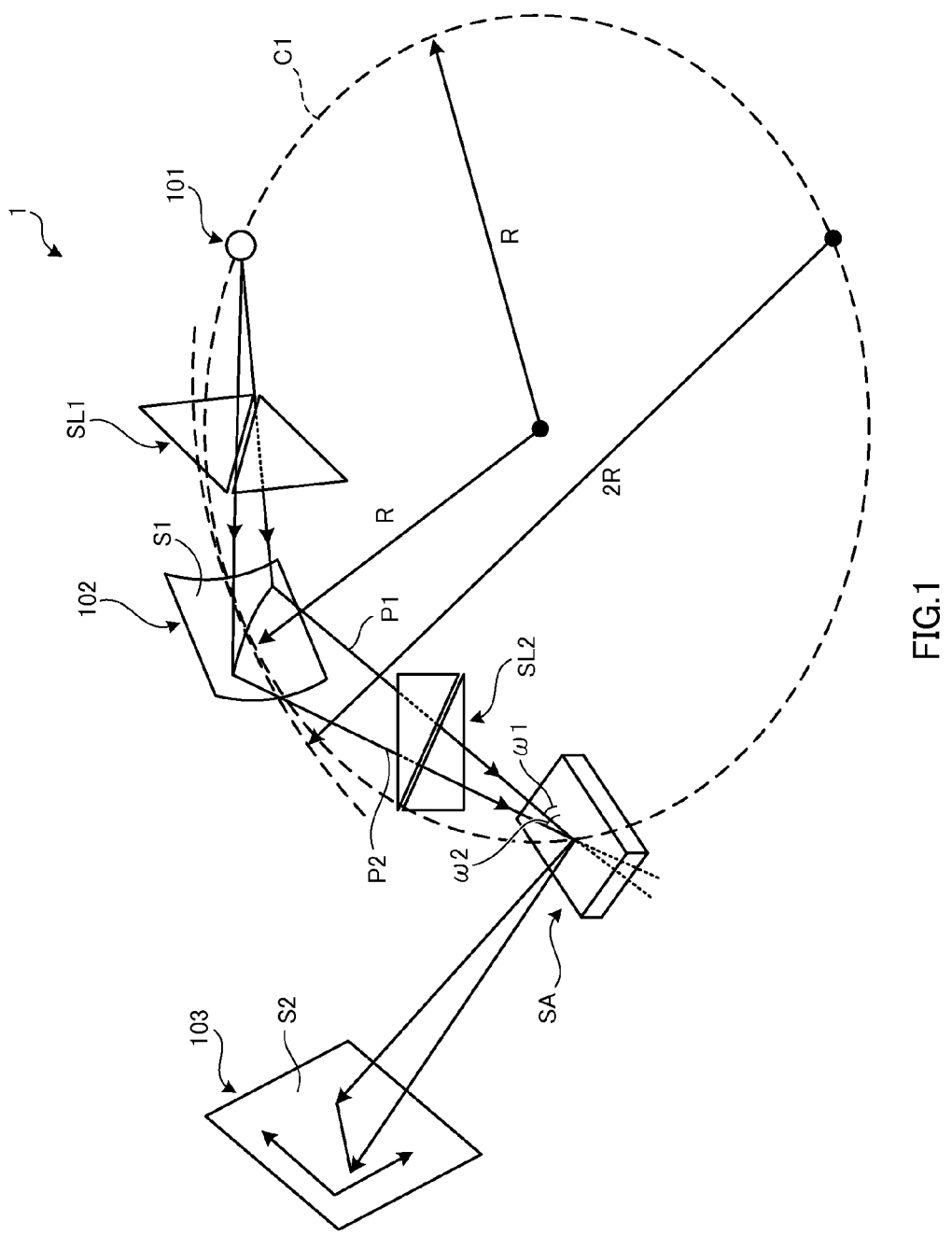
FIG. 1 is a schematic view illustrating a configuration example of a measuring apparatus used for a method for measuring a scattering intensity distribution according to the present embodiment.

FIG. 1 is a schematic view illustrating a configuration example of a measuring apparatus 1 used for a method for measuring a scattering intensity distribution according to the present embodiment. The measuring apparatus 1 is provided with an X-ray source 101 that radiates X-rays, a doubly-curved crystal (X-ray optical element) 102 that reflects only X-rays having a single wavelength (hereinafter referred to as "monochromatic X-rays") out of X-rays radiated from the X-ray source 101 and causes the reflected X-rays to be incident on a sample SA, and a two-dimensional detector 103 that detects monochromatic X-rays scattered by the sample SA. Slits SL1 and SL2 are arranged at a position between the X-ray source 101 and the doubly-curved crystal 102, and at a position between the doubly-curved crystal 102 and the sample SA respectively in order for monochromatic X-rays incident upon the sample SA to have a predetermined correlation.

The X-ray source 101 and the doubly-curved crystal 102 together with the sample SA are arranged on a circumference of an identical circle (Rowland circle) C1. As will be described later, the doubly-curved crystal 102 is curved at a predetermined curvature radius and has a monochromatization function that monochromatizes X-rays and a converging function (condensing function) that causes X-rays to converge in directions parallel and perpendicular to the plane including the Rowland circle C1. Through these functions, X-rays that are radiated from the X-ray source 101 and pass through the slit SL1 are reflected and monochromatized by the doubly-curved crystal 102, pass through the slit SL2 and converge on the sample SA on the Rowland circle C1. Although the present embodiment will describe a configuration example using the doubly-curved crystal 102, other X-ray optical elements having an X-ray converging function may also be used. The X-ray monochromatization function may also be implemented in other configurations.

The two-dimensional detector 103 is arranged at a given position at which scattering of monochromatic X-rays by the sample SA can be detected, and some of the monochromatic X-rays scattered by the sample SA are incident on the two-dimensional detector 103. Note that FIG. 1 shows the two-dimensional detector 103 arranged so as to simultaneously cover a range of X-ray scattering angles (angle formed between incident X-rays and scattered X-rays) of substantially 70° to 80°. The two-dimensional detector 103 is preferably disposed at a position where the distance from the sample SA is 0.3 to 5 times the distance from the X-ray source 101 to the doubly-curved crystal 102 (typically, 5 cm to 100 cm). Alternatively, the two-dimensional detector 103 may also be disposed at a position where the distance from the X-ray source 101 to the two-dimensional detector 103 falls within 2 m. Such an arrangement can reduce the scale of the measuring apparatus 1 and easily achieve required measurement resolution.

The X-ray source 101 is provided with an X-ray tube (not shown) that causes thermal electrons generated at a cathode to collide with an anticathode (anode) to generate X-rays. This X-ray tube causes characteristic X-rays ($K_\alpha$-rays, $K_\alpha$-rays) corresponding to a metal used for the anticathode. The X-rays radiated from the X-ray tube include white X-rays as a background in addition to characteristic X-rays. White X-rays are removed using a monochromator made of a single crystal or multilayer film or the like. In general, copper (Cu), molybdenum (Mo) or silver (Ag) is used for the anticathode of the X-ray tube and $K_\alpha$-rays thereof ($CuK_\alpha$-rays, $MoK_\alpha$-rays, $AgK_\alpha$-rays) are used for measurement thereof.

The slit SL1 is disposed in the traveling direction of the characteristic X-rays (typically, $K_\alpha$-rays) radiated from the X-ray source 101. The slit SL1 is disposed to be inclined with respect to the plane including the Rowland circle C1 so as to cause the monochromatic X-rays incident upon the sample SA to have a predetermined correlation. For this reason, only the components radiated in a predetermined in-plane direction of the X-rays radiated from the X-ray source 101 pass through the slit SL1 and are incident on the doubly-curved crystal 102 in the downstream. To be more specific, the slit SL1 allows to pass therethrough, only X-rays radiated in the predetermined in-plane direction inclined with respect to the plane including the Rowland circle C1. Note that the slit SL1 need not always be used when the intensity of the background can be kept to a low enough level by the slit SL2 interposed between the doubly-curved crystal 102 and the sample SA.

Figure 2:
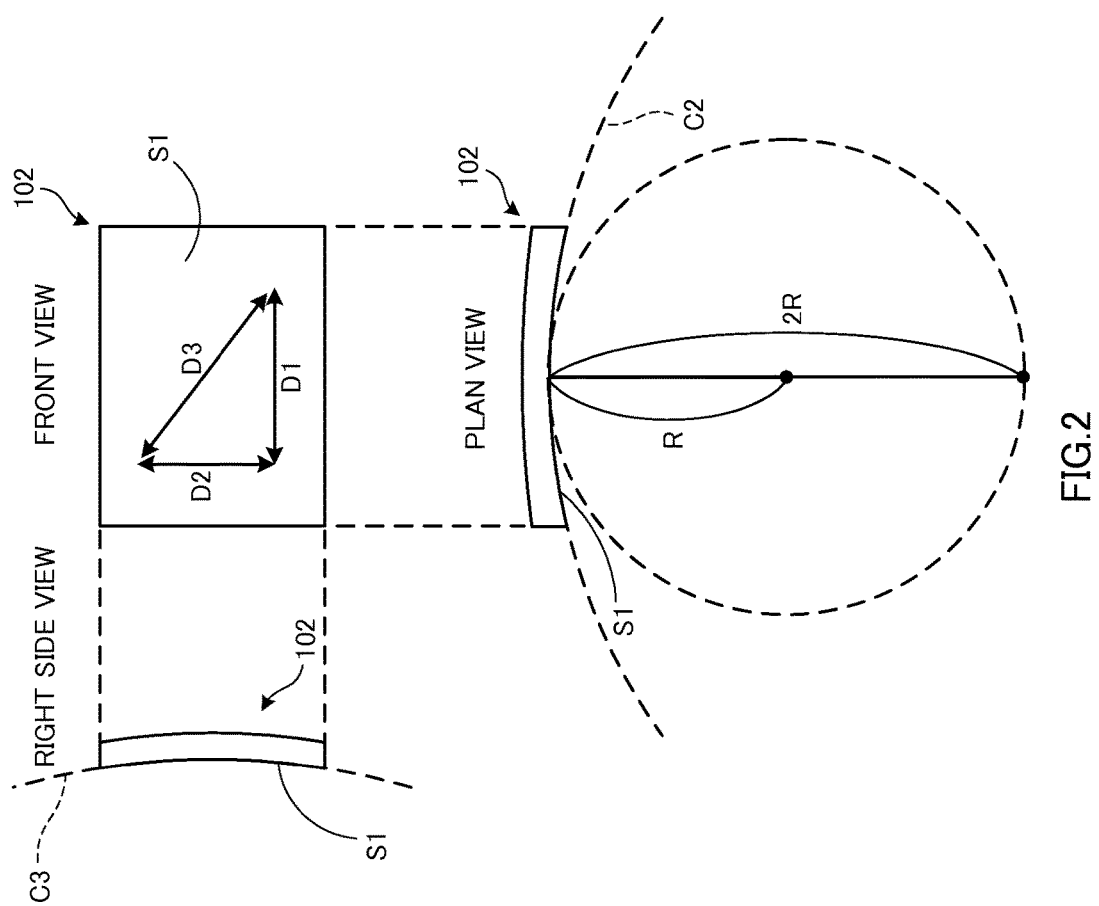
FIG. 2 is a schematic view illustrating a configuration example of a doubly-curved crystal.

FIG. 2 is a schematic view illustrating a configuration example (Johann type) of the doubly-curved crystal 102. In addition to a front view of a reflecting plane S1 of the doubly-curved crystal 102 viewed from the front, FIG. 2 shows a plan view and a right-side view thereof together, which are viewed from a direction perpendicular to the plane including the Rowland circle C1. As shown in FIG. 2, the doubly-curved crystal 102 has a curved shape obtained by curving a planar crystal at a predetermined curvature radius in a first direction D1 parallel to the plane including the Rowland circle C1 and a second direction D2 perpendicular to the plane including the Rowland circle C1.

The lattice plane of the doubly-curved crystal 102 is curved along a circle C2 (radius is 2R) having a radius twice that of the Rowland circle C1 (radius is R) in the first direction D1. That is, the lattice plane of the doubly-curved crystal 102 is curved at a curvature radius of 2R in the first direction D1. This gives the doubly-curved crystal 102 a converging function in the direction parallel to the plane including the Rowland circle C1. Furthermore, the lattice plane of the doubly-curved crystal 102 is curved along a circle C3 having a radius of $2R \sin^2\Theta$ ($\Theta$ is a Bragg angle of a single crystal making up the doubly-curved crystal 102) in the second direction D2. That is, the lattice plane of the doubly-curved crystal 102 is curved at a curvature radius of $2R \sin^2\Theta$ in the second direction D2. This gives the doubly-curved crystal 102 a converging function in a direction perpendicular to the plane including the Rowland circle C1. X-rays radiated from the X-ray source 101 disposed on the Rowland circle C1 is reflected by the reflecting plane S1 of the doubly-curved crystal 102 and caused to converge on the sample SA on the Rowland circle C1 two-dimensionally (directions parallel and perpendicular to the plane including the Rowland circle C1).

This doubly-curved crystal 102 is made of a material such as graphite, silicon, germanium or copper. The doubly-curved crystal 102 made of silicon in particular includes few defects and is easily available, and is therefore preferable from the standpoint that it is possible to implement the measuring apparatus 1 of high performance at a low cost.

The slit SL2 similar to the slit SL1 is disposed in the traveling direction of the monochromatic X-rays reflected by the doubly-curved crystal 102. The slit SL2 is also disposed to be inclined with respect to the plane including the Rowland circle C1 so as to cause the monochromatic X-rays incident upon the sample SA to have a predetermined correlation. For this reason, only the components radiated in a predetermined in-plane direction of the monochromatic X-rays reflected by the doubly-curved crystal 102 pass through the slit SL2 and are incident on the sample SA. Note that for a measuring apparatus in which the Rowland circle C1 is not defined, the slit SL2 may be disposed to be inclined with respect to a predetermined reference plane (e.g., reference plane B1, or plane V1 shown in FIG. 3).

The monochromatic X-rays incident upon the sample SA are scattered by atoms (electrons) making up the crystal lattice of the sample SA. Some of the scattered X-rays are incident on the two-dimensional detector 103. The two-dimensional detector 103 is provided with a light receiving surface S2 having a predetermined area and is constructed so as to be able to detect a relationship between an incident position and intensity of monochromatic X-rays. A scattering intensity distribution of X-rays from the sample SA in a range of a predetermined scattering direction is detected by this two-dimensional detector 103. The detected scattering intensity distribution is coordinate-transformed by a calculation section (not shown) of the measuring apparatus 1 and a scattering intensity distribution in a reciprocal space is calculated.

As shown in FIG. 1, when X-rays radiated from the X-ray source 101 are incident on the slit SL1, the slit SL1 causes to pass therethrough, only the X-rays radiated in the in-plane direction inclined with respect to the Rowland circle C1. Thus, the reflecting plane S1 of the doubly-curved crystal 102 is irradiated with a linear X-ray beam along a third direction D3 inclined with respect to the first direction D1 and the second direction D2 as shown in FIG. 2.

As described above, the doubly-curved crystal 102 is curved at a predetermined curvature radius and monochromatic X-rays reflected by the doubly-curved crystal 102 are caused to converge on the sample SA on the Rowland circle C1 via the slit SL2. For this reason, the monochromatic X-rays reflected by the doubly-curved crystal 102 and incident upon the sample SA are caused to be incident on the sample SA at a glancing angle (complementary angle of the angle of incidence) ω which varies depending on the path from the X-ray source 101. For example, a monochromatic X-ray that arrives at the sample SA along a path P1 is incident on the sample SA at a glancing angle w1 and a monochromatic X-ray that arrives at the sample SA along a path P2 is incident on the sample SA at a glancing angle w2.

Figure 3:
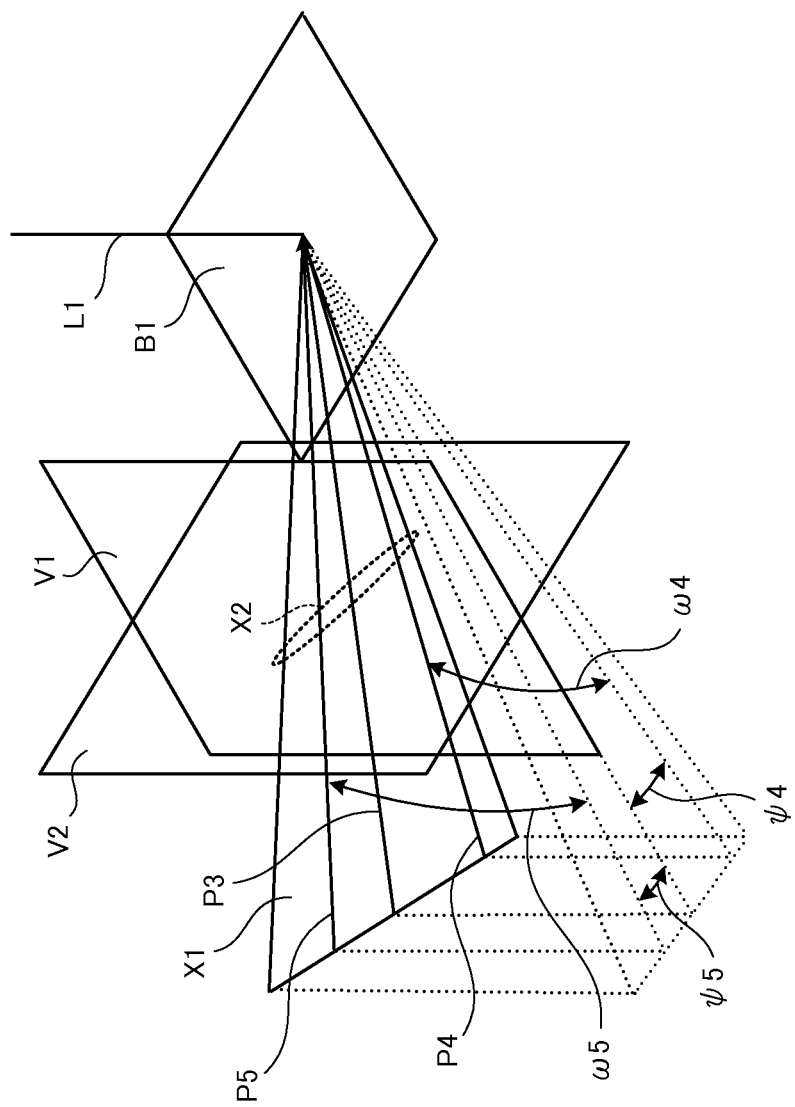
FIG. 3 is a schematic view for describing monochromatic X-rays incident upon a sample.

Monochromatic X-rays incident upon the sample SA are given a predetermined correlation via the slits SL1 and SL2. FIG. 3 is a schematic view for describing monochromatic X-rays incident upon the sample SA. As shown in FIG. 3, by passing through the slits SL1 and SL2, a surface X1 along which the X-ray beam propagates is inclined at a given angle with respect to a reference plane B1 and a plane V1 perpendicular to the reference plane B1. The plane V1 is typically a plane including an X-ray path P3 located in the center of an X-ray converging angle and the normal L1 of the reference plane B1. The reference plane B1 is, for example, a lattice plane involved with X-ray diffraction on the sample SA, but the surface of the sample SA may also be used as the reference plane B1. In addition, the plane including the Rowland circle C1 may also be used as the reference plane B1.

As shown in FIG. 3, since the surface X1 along which the X-ray beam propagates is inclined, a projected pattern X2 of the X-ray beam projected onto the plane V2 perpendicular to the reference plane B1 and the plane V1 becomes an inclined straight line. That is, a correlation is given between the angle formed by the projected pattern X2 with respect to the reference plane B1 and the angle (corresponding to glancing angle w) formed by the traveling direction of the monochromatic X-rays with respect to the reference plane B1. Moreover, a correlation is given between an angle (corresponding to a glancing angle ω4, ω5) formed by each path of converging X-rays after a plurality of paths (e.g., path P4,P5) with respect to the reference plane B1 and an angle (corresponding to angle ω4, ω5) formed by each path with respect to the plane including the path P3 located in the center of the respective paths and the normal L1 of the reference plane B1. By giving such correlations, it is possible to perform subsequent coordinate transformations appropriately.

Note that the slit SL2 is assumed to have a linear shape to give the X-ray beam a linear (first-order) correlation, but the slit SL2 is not limited to the linear shape. For example, the slit SL2 may have a parabolic shape to give a second-order correlation. The slit SL2 can take any shape if the surface X1 of the X-ray beam is at least not parallel or perpendicular to the reference plane B1. For example, it is possible to set the angle of inclination of the surface X1 with respect to the plane V1 to 5° to 85° and preferably 15° to 75°.

Thus, if monochromatic X-rays having predetermined correlations are caused to be incident on the sample SA at different glancing angles ω, it is possible to cause scattering corresponding to a plurality of conditions with different glancing angles ω to occur at a time. X-rays scattered by the sample SA are incident on the two-dimensional detector 103 placed downstream of the sample SA at different positions according to the glancing angle ω and the scattering angle 2θ. For this reason, since the two-dimensional detector 103 detects this scattering at a time, scanning in the glancing angle direction (ω direction) is unnecessary. Since the two-dimensional detector 103 is configured to be able to measure a wide scattering angle 2θ at a time, scanning in the scattering angle direction (2θ direction) is also unnecessary.

Figure 4:
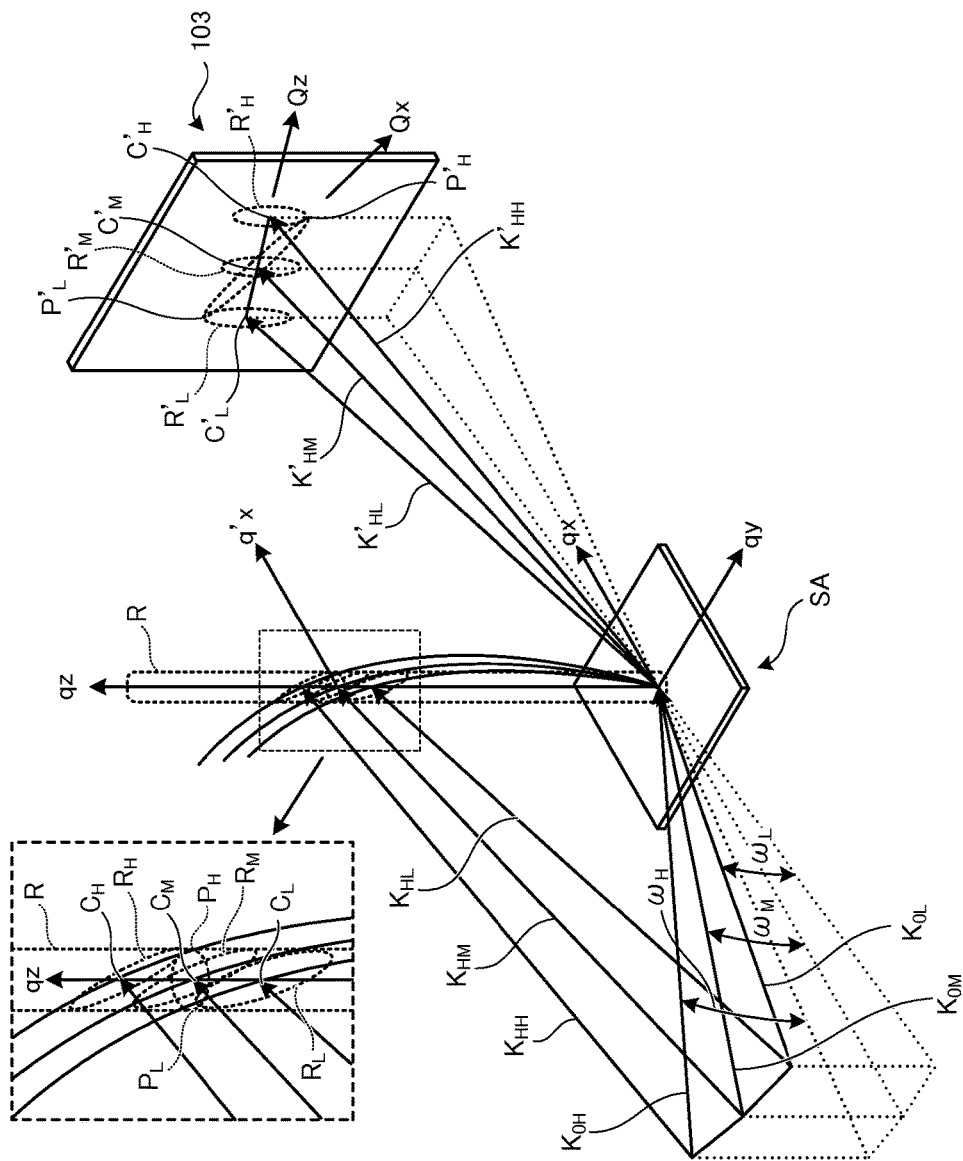
FIG. 4 is a schematic view illustrating how monochromatic X-rays having a predetermined correlation are incident on a sample at different glancing angles in correspondence with respective optical paths and how scattered X-rays are incident on a two-dimensional detector.

FIG. 4 is a schematic view illustrating how the monochromatic X-rays having the aforementioned predetermined correlations are caused to be incident on the sample SA at different glancing angles ω in correspondence to the respective optical paths and how the scattered X-rays are incident on the two-dimensional detector. FIG. 4 describes a schematic view where the two-dimensional detector 103 is disposed so as to simultaneously cover a range of scattering angles of X-rays (angle formed by incident X-rays and scattered X-rays) of substantially 5° to 15°. FIG. 4 schematically shows situations of the reciprocal space and real space. The sample SA is assumed to be a semiconductor having a superlattice structure. In the reciprocal space shown on the left side of FIG. 4, if an end of a wave number vector of a scattered wave is positioned to be a rod part R that extends from the origin O in the qz direction, the scattering intensity of X-rays becomes strong. More specifically, the scattering intensity of X-rays becomes strong under the condition under which the Ewald sphere and the rod part R intersect with each other.

FIG. 4 shows $K_{OH}$, $K_{OM}$ and $K_{OL}$ as wave number vectors of X-rays incident upon the sample SA at glancing angles $\omega_H$, $\omega_M$ and $\omega_L$. Since the scattering intensities of X-rays become stronger under a condition under which the Ewald sphere and the rod part R intersect with each other, the scattering intensities of X-rays $K_{OH}$, $K_{OM}$ and $K_{OL}$ incident upon the sample SA become stronger in regions $R_H$, $R_M$ and $R_L$ where the Ewald sphere and the rod part R intersect with each other. When vectors connecting points of intersection between the center line of the rod part R (that is, qz-axis) and the Ewald sphere and starting points of $K_{OH}$, $K_{OM}$ and $K_{OL}$ are assumed to be $K_{HH}$, $K_{HM}$ and $K_{HL}$, the plane including $K_{OH}$ and $K_{HH}$, the plane including $K_{OM}$ and $K_{HM}$, and the plane including $K_{OL}$ and $K_{HL}$ (scattering surfaces) are inclined to each other.

In a real space shown on the right of FIG. 4, the scattered X-rays are caused to be incident on the two-dimensional detector 103. The X-rays caused to be incident on the sample SA as $K_{OH}$, $K_{OM}$ and $K_{OL}$ are scattered centered on directions shown by $K'_{HH}$, $K'_{HM}$ and $K'_{HL}$, and projected onto regions $R'_H$, $R'_M$ and $R'_L$ shown by ellipses on the two-dimensional detector 103. In this case, points $C_H$, $C_M$ and $C_L$ along the center line (qz-axis) of the rod part R in the reciprocal space are recorded as C'H, C'M and C'L on the two-dimensional detector 103. End points $P_H$ and $P_L$ in a direction parallel to qx in a cross section of the rod part R parallel to the qx-qy plane are recorded as $P'_H$ and $P'_L$ on the two-dimensional detector 103.

In the two-dimensional detector 103, the intensity distribution on a straight line including $C'_H$, $C'_M$ and $C'_L$ reflects the scattering intensity (that is, scattering intensity in the qz-axis direction) on a straight line including $C_H$, $C_M$ and $C_L$ in the reciprocal space. Furthermore, in the two-dimensional detector 103, the intensity distribution on a straight line including $P'_H$, $C'_M$ and $P'_L$ reflects the scattering intensity (that is, scattering intensity in the qx-axis direction) on a straight line including $P_H$, $C_M$ and $P_L$ in the reciprocal space. For this reason, by coordinate-transforming the straight line direction (Qz-axis) including $C'_H$, $C'_M$ and $C'_L$ and the straight line direction (Qx-axis) including $P'_H$, $C'_M$ and $P'_L$ into the qz-axis and the qx-axis respectively, it is possible to obtain a scattering intensity distribution within the qx-qz plane in the reciprocal space. That is, it is possible to measure a scattering intensity distribution within the qx-qz plane in the reciprocal space without performing scanning in the ω direction and the 2θ direction.

Figure 5B:
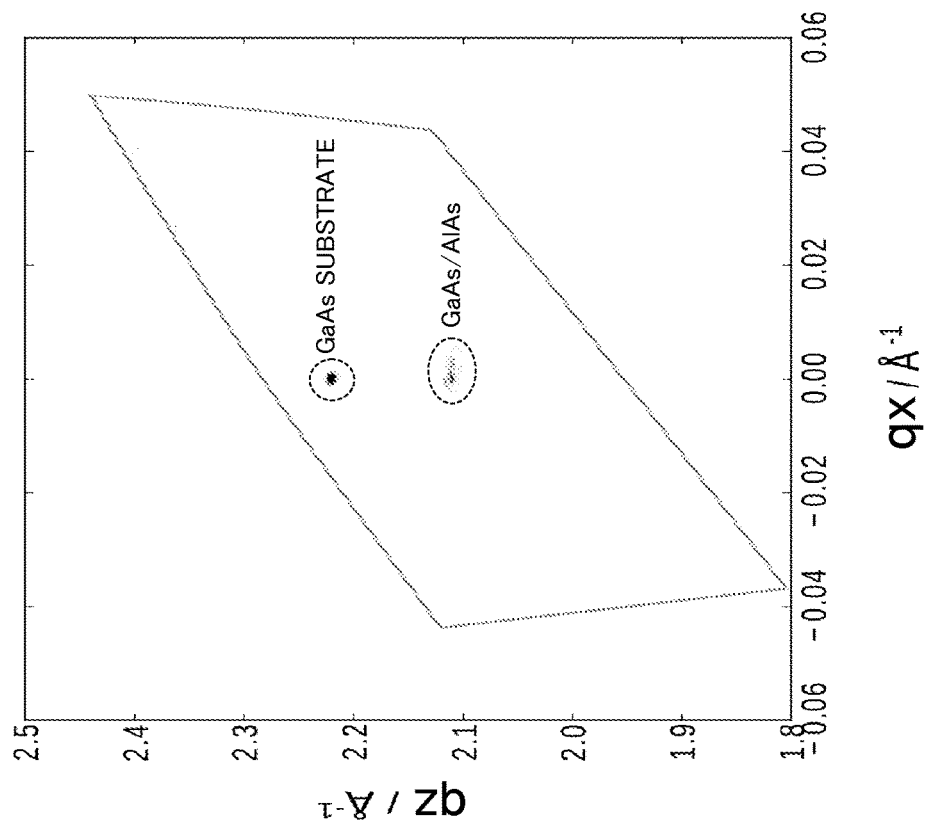
FIG. 5 is a schematic view illustrating a scattering intensity distribution obtained by measuring a sample having a superlattice structure using the method for measuring a scattering intensity distribution according to the present embodiment.
Figure 5A:
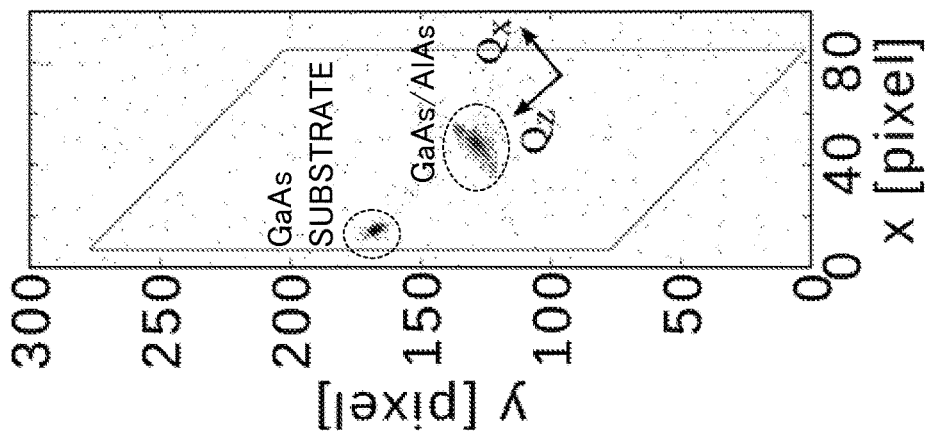
Figure 6B:
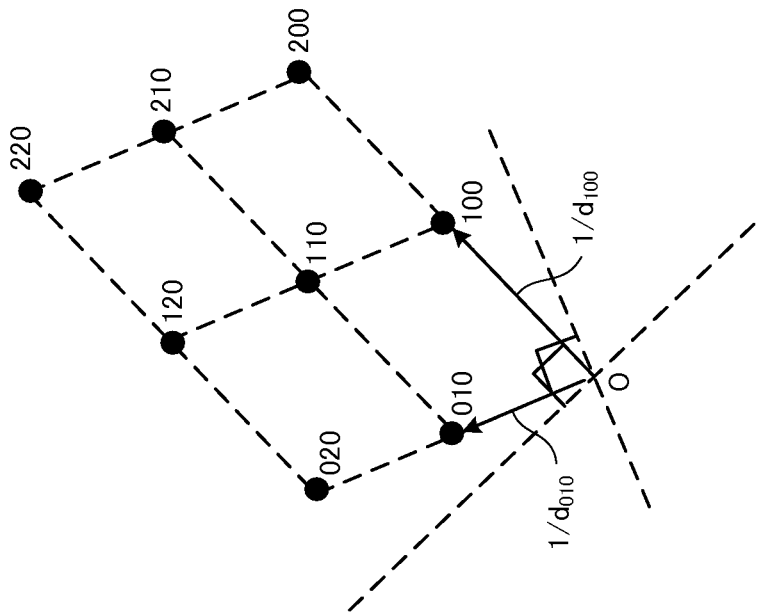
FIG. 6 is a schematic view illustrating a relationship between a real space and a reciprocal space.
Figure 6A:
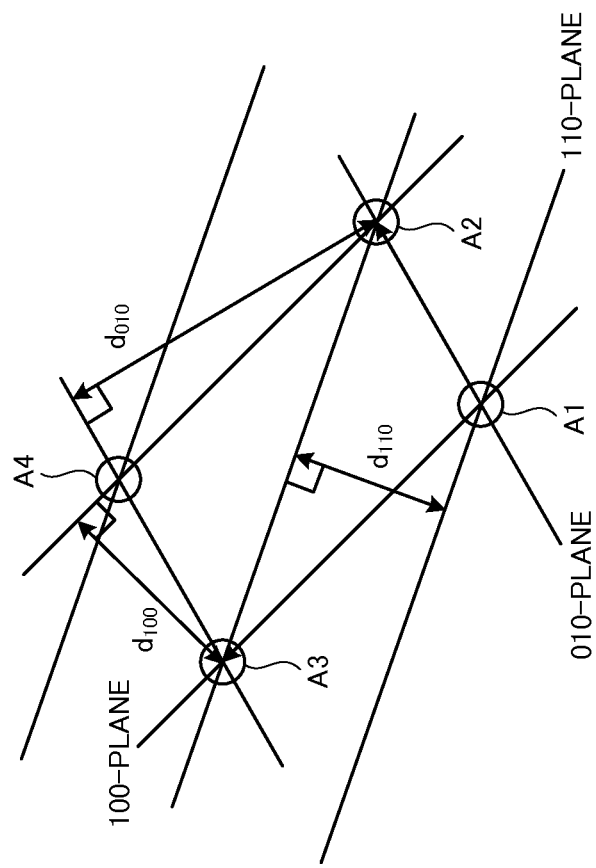
Figure 7:
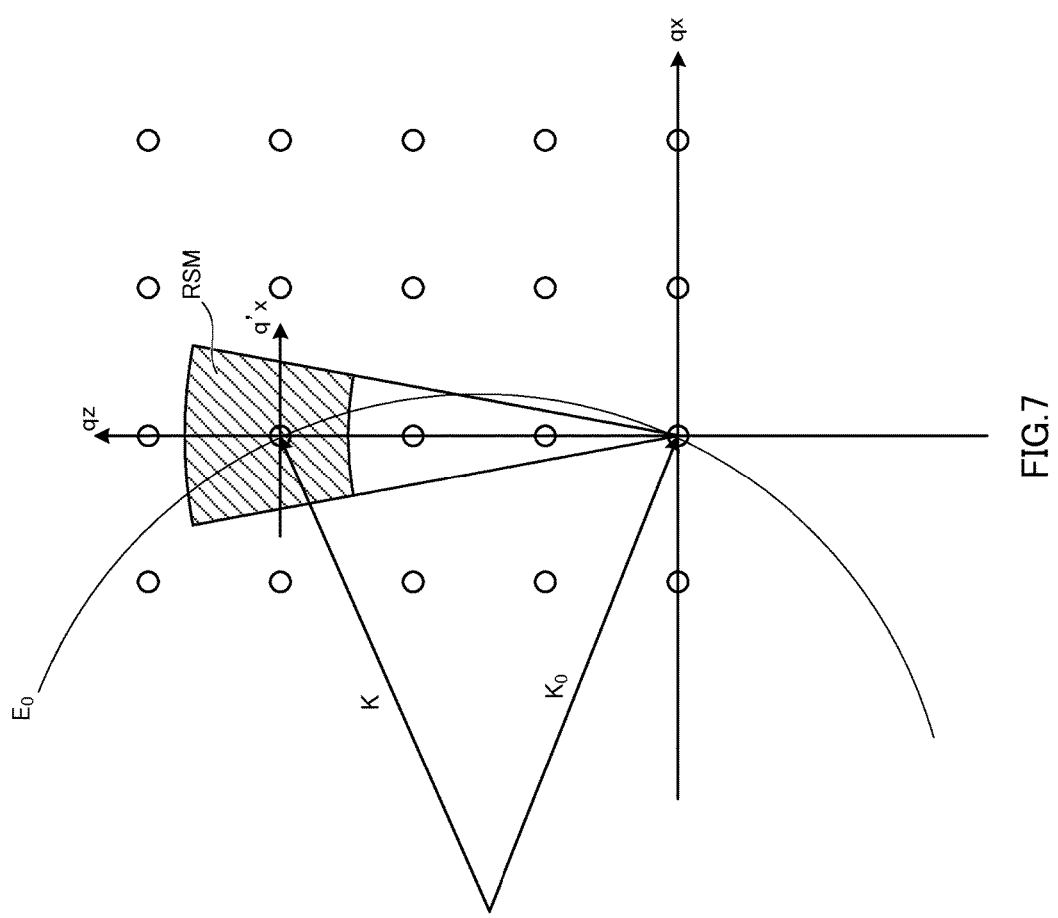
FIG. 7 is a schematic view illustrating a relationship between a reciprocal lattice point and an Ewald sphere.
Figure 8:
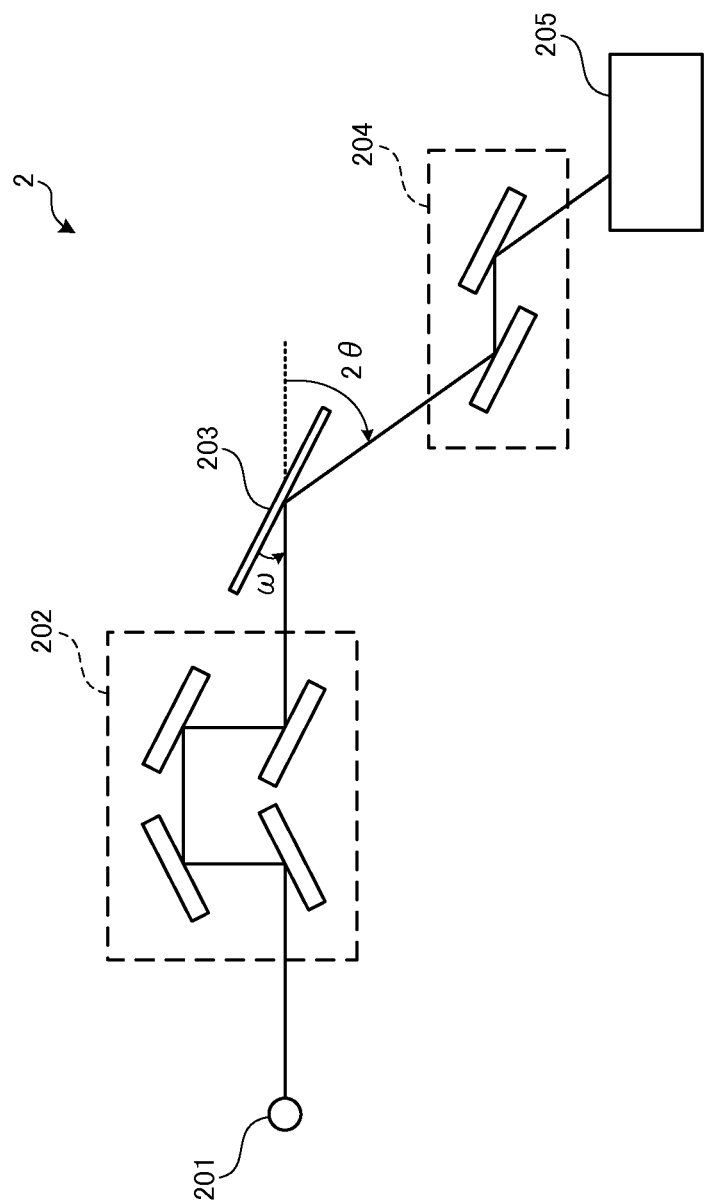
FIG. 8 is a schematic view illustrating a configuration example of a measuring apparatus used for reciprocal space mapping.
Figure 9:
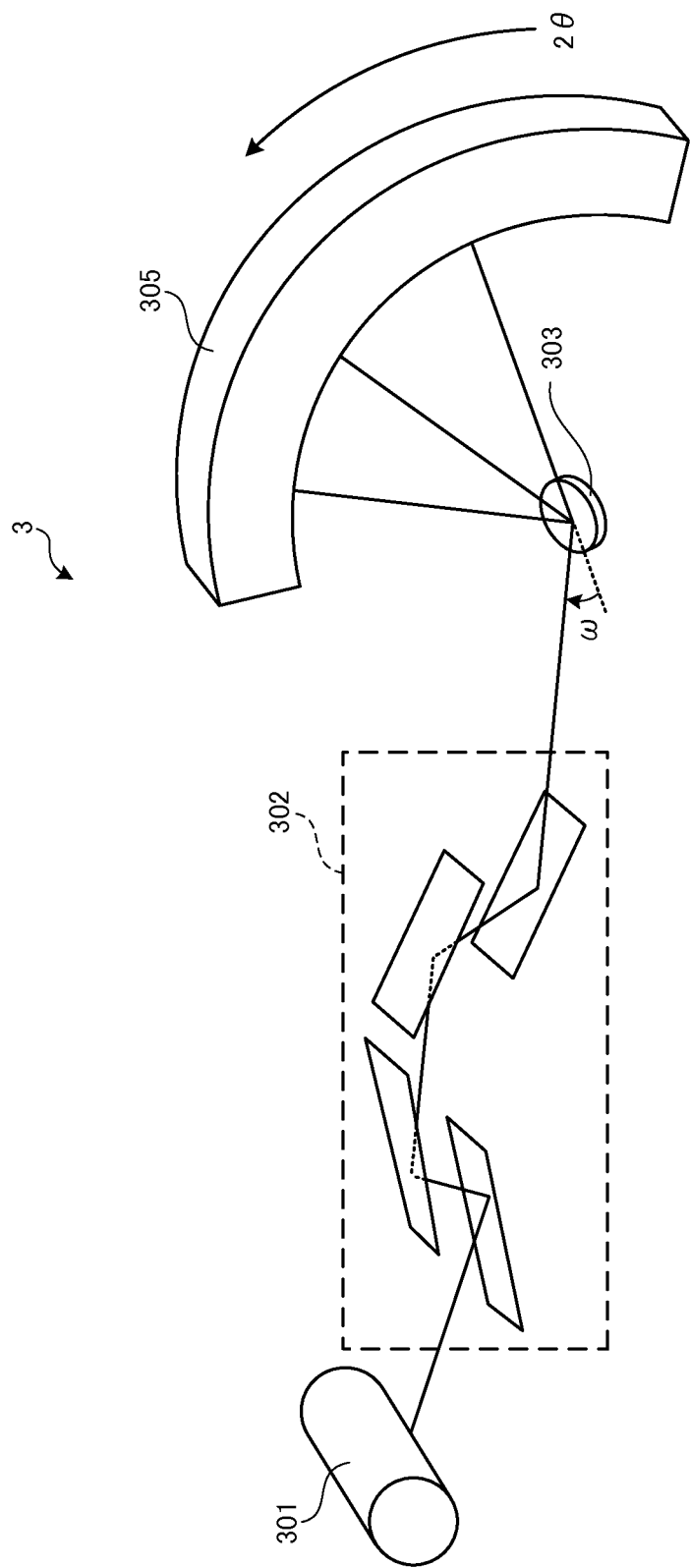
FIG. 9 is a schematic view illustrating another configuration example of the measuring apparatus used for reciprocal space mapping.

FIG. 5 is a diagram illustrating measurement results of a scattering intensity distribution obtained when measuring a sample having a superlattice structure using the method for measuring a scattering intensity distribution according to the present embodiment and illustrates a scattering intensity distribution of the sample in which AlAs/GaAs superlattice structure is formed on a GaAs substrate. Here, CuKα1 characteristic X-rays obtained by operating the X-ray source 101 under a condition of 50 kV, 60 mA are used as monochromatic X-rays and PILATUS100K manufactured by DECTRIS Ltd., Switzerland is used as the two-dimensional detector 103. FIG. 5A illustrates the scattering intensity distribution on the two-dimensional detector 103 detected using the aforementioned method and FIG. 5B illustrates the coordinate-transformed scattering intensity distribution. The vertical axis and the horizontal axis in FIG. 5A denote pixel positions of the two-dimensional detector 103 and the vertical axis and the horizontal axis in FIG. 5B denote transfer momentum qz and qx (unit is $Å^{-1}$ for both). In monochromatic X-rays radiated onto the sample SA, the converging angle (condensing angle) in the in-plane direction including the Rowland circle is small (e.g., on the order of $\pm 2°$). For this reason, the scattering intensity distribution in FIG. 5A obtained using the above-described method can be approximated as scattering power within the qx-qz plane in the reciprocal space. The measurement results shown in FIG. 5 are obtained in a measurement time of as few as 10 seconds. In this way, it is apparent that the method for measuring a scattering intensity distribution according to the present embodiment allows the scattering intensity distribution in the reciprocal space to be measured in a short time.

The coordinate system of the scattering intensity distribution detected by the two-dimensional detector 103 is associated with the coordinate system of the scattering intensity distribution in the reciprocal space. To be more specific, the qx direction in the reciprocal space corresponds to the Qx direction in FIG. 5A and the qz direction in the reciprocal space corresponds to the Qz direction in FIG. 5A. For this reason, by coordinate-transforming Qx and Qz into qx and qz respectively, it is possible to obtain the scattering intensity distribution in the reciprocal space shown in FIG. 5B. Since this correspondence depends on a correlation given to monochromatic X-rays, for example, the calculation section (not shown) in the measuring apparatus 1 can perform coordinate transformation based on the correlation.

As described above, according to the method and apparatus for measuring a scattering intensity distribution according to the present embodiment, the monochromatic X-rays are caused to be incident on the sample at different glancing angles ω at a time in a state in which there is a correlation between an angle formed by each optical path of the X-rays condensed after passing through a plurality of optical paths with respect to a reference plane and an angle formed by each optical path with respect to a plane including an optical path located in the center of the respective optical paths and the normal of the reference plane, and the two-dimensional detector 103 detects the scattering intensity of the monochromatic X-rays scattered by the sample SA, and therefore scanning in both the glancing angle direction (ω direction) and the scattering angle direction (2θ direction) becomes unnecessary. That is, by causing the monochromatic X-rays to be incident on the sample SA at different glancing angles ω at a time, it is possible to cause scattering corresponding to a plurality of conditions with different glancing angles ω to occur at a time, and the two-dimensional detector 103 can thereby detect scattering corresponding to a plurality of conditions with different glancing angle ω and scattering angle 2θ values at a time. It is thereby possible to measure a scattering intensity distribution in the reciprocal space in a short time.

Furthermore, according to the method and apparatus for measuring a scattering intensity distribution according to the present embodiment, the X-ray source 101, doubly-curved crystal (X-ray optical element) 102, and sample SA are arranged along the Rowland circle C1, and it is thereby possible to cause monochromatic X-rays radiated from the X-ray source 102 to be incident on the sample SA via the doubly-curved crystal 102 appropriately. Since characteristic X-rays are used as the monochromatic X-rays, compared to the case where white X-rays from synchrotron radiation or the like are used, the configuration of the X-ray source 101 is simplified and the cost involved with measurement of the scattering intensity distribution can be reduced. Moreover, since the doubly-curved crystal 102 is used as the X-ray optical element for causing monochromatic X-rays to reflect and converge, it is easy to cause monochromatic X-rays to be incident on the sample SA at different glancing angles ω at a time.

It should be noted that the present invention is not limited to the above-described embodiment, but can be implemented and modified in various ways. For example, the above-described embodiment shows a method and configuration in which the calculation section provided in the measuring apparatus 1 performs coordinate transformation, but, for example, coordinate transformation may also be performed by an outside calculation apparatus. In the case where the scattering intensity distribution detected by the two-dimensional detector can be directly used, coordinate transformation need not always be performed. In such cases, the calculation section of the measuring apparatus 1 can be omitted.

The above-described embodiment shows a configuration in which the X-ray tube is provided as the X-ray source 101, but the configuration of the X-ray source 101 is not particularly limited. For example, the X-ray source 101 may be a secondary X-ray source that somehow condenses X-rays emitted from another X-ray source into a dotted or linear shape. Similarly, the configuration of the X-ray optical element is not particularly limited if it is provided with the X-ray converging function described in the embodiment. For example, instead of the doubly-curved crystal 102, a crystal in which twisting in a direction perpendicular to the curving direction of a singly-curved crystal is further added (bent-twisted crystal) or the like may be used. In the measuring apparatus 1 for which the Rowland circle C1 is not defined, an X-ray optical element may be used which has at least a correlation between an angle formed between the lattice plane (reference plane B1) involved with diffraction of the sample SA and the optical path of X-rays, and an angle formed between the plane V1 and the optical path of X-rays, and which includes a converging function (condensing function) toward the surface of the sample SA.

Furthermore, using a measuring apparatus using a linear X-ray source, a monochromator crystal and a fan-shaped multi-slit that causes a linear X-ray source to converge in a vertical direction or capillary tube, it is also possible to perform similar measurement by forming an X-ray beam having a correlation between an angle formed between the lattice plane (reference plane B1) involved with diffraction of the sample SA and the optical path of X-rays, and an angle formed between the plane V1 and the optical path of X-rays. Moreover, the present invention can be implemented by changing an arrangement of each component, size and shape or the like in the above embodiment as appropriate. The present invention can also be implemented by changing other aspects as appropriate.

The present invention is useful, for example, when irradiating a sample with X-rays and measuring a scattering intensity distribution in a reciprocal space.

The present application is based on Japanese Patent Application No. 2012-273064 filed on Dec. 14, 2012, entire content of which is expressly incorporated by reference herein.

What is claimed is:

1. A method for measuring a scattering intensity distribution, comprising:
   reflecting X-rays emitted from an X-ray source by an X-ray optical element so as to converge in a vicinity of a surface of a sample;
   causing monochromatic X-rays to pass through a plurality of optical paths to the sample at glancing angles that differ depending on the respective optical paths, at a time with correlation that a plane along which the X-rays propagate is inclined at a given angle with respect to a reference plane and is inclined at a given angle with respect to a plane including a central optical path among the optical paths and a normal of the reference plane;
   detecting scattering intensities of the monochromatic X-rays scattered by the sample using a two-dimensional detector; and
   coordinate-transforming the scattering intensities detected by the two-dimensional detector based on the correlation thereby to measure the scattering intensity distribution in a reciprocal space.

2. The method for measuring a scattering intensity distribution according to claim 1, wherein the X-ray source, the X-ray optical element, and the sample are arranged along an identical circumference.

3. The method for measuring a scattering intensity distribution according to claim 2, wherein the reference plane is a plane including the circumference.

4. The method for measuring a scattering intensity distribution according to claim 1, wherein the reference plane is the surface of the sample.

5. The method for measuring a scattering intensity distribution according to claim 1, wherein characteristic X-rays are used as the X-rays.

6. The method for measuring a scattering intensity distribution according to claim 1, wherein a doubly-curved crystal or bent-twisted crystal is used as the X-ray optical element.

7. A measuring apparatus comprising:
   an X-ray source;
   an X-ray optical element which reflects X-rays emitted from an X-ray source so as to converge in a vicinity of a surface of a sample;
   a two-dimensional detector detect the scattering intensities of the monochromatic which coordinate-transforms the scattering intensities detected by the two-dimensional detector based on the correlation thereby to measure the scattering intensity distribution in a reciprocal space; and
   wherein monochromatic X-rays cause to pass through a plurality of optical paths to the sample at glancing angles that differ depending on the respective optical paths, at a time with correlation that a plane along which the X-rays propagate is inclined at a given angle with respect to a reference plane and is inclined at a given angle with respect to a plane including a central optical path among the optical paths and a normal of the reference plane.

8. The measuring apparatus according to claim 7, wherein the X-ray source, the X-ray optical element, and the sample are arranged along an identical circumference.

9. The measuring apparatus according to claim 8, wherein the reference plane is a plane including the circumference.

10. The measuring apparatus according to claim 7, wherein the reference plane is the surface of the sample.

11. The measuring apparatus according to claim 7, wherein the X-ray source is configured to be able to generate characteristic X-rays.

12. The measuring apparatus according to claim 7, wherein the X-ray optical element is a doubly-curved crystal or bent-twisted crystal.

* * * * *